(12) United States Patent
Nelson et al.

(10) Patent No.: US 11,097,141 B2
(45) Date of Patent: Aug. 24, 2021

(54) SYSTEMS, APPARATUSES, AND METHODS FOR RENDERING DRUGS UNUSABLE, IRRETRIEVABLE, AND SUITABLE FOR NON-REGULATED WASTE DISPOSAL

(71) Applicant: Vigilant Waste Technologies, Inc., Austin, TX (US)

(72) Inventors: David A. Nelson, Austin, TX (US); Alfred Rafi Baddour, Austin, TX (US)

(73) Assignee: Vigilant Waste Technologies, Inc., Austin, TX (US)

( * ) Notice: Subject to any disclaimer, the term of this patent is extended or adjusted under 35 U.S.C. 154(b) by 0 days.

(21) Appl. No.: 16/205,506

(22) Filed: Nov. 30, 2018

(65) Prior Publication Data
US 2019/0091504 A1 Mar. 28, 2019

Related U.S. Application Data

(62) Division of application No. 15/064,773, filed on Mar. 9, 2016, now Pat. No. 10,155,127, which is a division
(Continued)

(51) Int. Cl.
*A62D 3/30* (2007.01)
*A62D 3/33* (2007.01)
(Continued)

(52) U.S. Cl.
CPC ............. *A62D 3/33* (2013.01); *A61M 5/3278* (2013.01); *A62D 3/30* (2013.01); *A61C 11/00* (2013.01);
(Continued)

(58) Field of Classification Search
CPC ......... A62D 3/33; A62D 3/30; A61M 5/3278; A61M 2005/3282; B09B 3/0075; A61C 11/00; B02C 19/0075
See application file for complete search history.

(56) References Cited

U.S. PATENT DOCUMENTS 4,816,307 A * 3/1989 Honeycutt ............ B09B 3/0075
206/366
4,900,500 A 2/1990 Honeycutt
(Continued)

FOREIGN PATENT DOCUMENTS

WO 01/08824 2/2001

OTHER PUBLICATIONS

Nelson et al., "Systems, Apparatuses, And Methods For Rendering Drugs Unusable, Irretrievable, And Suitale For Waste Disposal", U.S. Appl. No. 14/252,499, filed Apr. 14, 2014, Office Action dated May 13, 2015, 6 pgs.
(Continued)

*Primary Examiner* — Jason K Niesz
(74) *Attorney, Agent, or Firm* — Egan, Enders & Huston LLP.

(57) ABSTRACT

Apparatuses and systems are provided which include one or more receptacles for receiving drugs and further include one or more stored supplies of one or more absorbent materials comprising crosslinkers, wherein the apparatus and systems are adapted to release the absorbent materials comprising crosslinkers into the one or more receptacles. A method is provided which includes depositing a drug into a predetermined amount of fluid and adding to the drug containing fluid a absorbent material comprising crosslinkers which is capable of encapsulating the drug containing fluid and possibly killing infectious materials within the fluid and/or denaturing the drug within the fluid.

35 Claims, 6 Drawing Sheets

Related U.S. Application Data of application No. 14/252,499, filed on Apr. 14, 2014, now Pat. No. 9,302,134.

(60) Provisional application No. 61/811,508, filed on Apr. 12, 2013.

(51) Int. Cl.
*A61M 5/32* (2006.01)
*B09B 3/00* (2006.01)
*B02C 19/00* (2006.01)
*A61C 11/00* (2006.01)

(52) U.S. Cl.
CPC .. *A61M 2005/3282* (2013.01); *B02C 19/0075* (2013.01); *B09B 3/0075* (2013.01)

(56) References Cited

U.S. PATENT DOCUMENTS

| | | | |
|---|---|---|---|
| 5,038,929 | A | 8/1991 | Kubofcik |
| 5,213,884 | A | 5/1993 | Fellows |
| 6,010,444 | A | 1/2000 | Honeycutt et al. |
| 6,203,484 | B1 | 3/2001 | Lepore et al. |
| 6,592,768 | B1 | 7/2003 | Lepore et al. |
| 6,868,344 | B1 * | 3/2005 | Nelson .......... G01N 21/31 702/31 |
| 7,120,487 | B2 | 10/2006 | Nelson |
| 7,184,897 | B2 | 2/2007 | Nelson |
| 7,458,741 | B2 | 12/2008 | Detwiler et al. |
| 7,673,825 | B2 | 3/2010 | Jeansonne et al. |
| 8,195,328 | B2 * | 6/2012 | Mallett .......... A61L 11/00 700/236 |
| 8,348,056 | B2 | 1/2013 | Maness |
| 8,490,795 | B2 | 7/2013 | Ziemba |
| 8,534,459 | B2 | 9/2013 | Maness |
| 8,573,426 | B2 | 11/2013 | Maness |
| 8,616,397 | B2 | 12/2013 | Maness |
| 8,684,968 | B2 | 4/2014 | Genosar |
| 9,302,134 | B1 | 4/2016 | Nelson et al. |
| 9,456,958 | B2 | 10/2016 | Reddy et al. |
| 10,155,127 | B1 | 12/2018 | Nelson et al. |
| 2006/0259195 | A1 * | 11/2006 | Eliuk ............ B65B 55/16 700/245 |
| 2008/0058736 | A1 | 3/2008 | Reshamwala |
| 2012/0088951 | A1 | 4/2012 | Deryck et al. |
| 2012/0305132 | A1 | 12/2012 | Maness |
| 2012/0323061 | A1 | 12/2012 | Stalons |
| 2014/0008259 | A1 | 1/2014 | Maness |

OTHER PUBLICATIONS

Nelson et al., "Systems, Apparatuses, And Methods For Rendering Drugs Unusable, Irretrievable, And Suitale For Waste Disposal", U.S. Appl. No. 14/252,499, filed Apr. 14, 2014, Office Action dated Sep. 4, 2015, 6 pgs.

Nelson et al., "Systems, Apparatuses, And Methods For Rendering Drugs Unusable, Irretrievable, And Suitale For Waste Disposal", U.S. Appl. No. 14/252,499, filed Apr. 14, 2014, Notice of Allowance dated Nov. 24, 2015, 5 pgs.

US Patent and Trademark Office, Notice of Allowance for U.S. Appl. No. 16/013,315 dated Dec. 4, 2018, 7 pages.

US Patent and Trademark Office, Notice of Allowance for U.S. Appl. No. 15/064,773 dated Aug. 9, 2018, 7 pages.

US Patent and Trademark Office, Office Action for U.S. Appl. No. 15/472,528 dated Nov. 17, 2017, 11 pages.

US Patent and Trademark Office, Notice of Allowance for U.S. Appl. No. 15/472,528 dated Apr. 26, 2018, 7 pages.

* cited by examiner

SYSTEMS, APPARATUSES, AND METHODS FOR RENDERING DRUGS UNUSABLE, IRRETRIEVABLE, AND SUITABLE FOR NON-REGULATED WASTE DISPOSAL

PRIORITY CLAIM

This application is a divisional of U.S. patent application Ser. No. 15/064,773, filed on Mar. 9, 2016, which is a divisional of U.S. patent application Ser. No. 14/252,499, filed on Apr. 14, 2014, now U.S. Pat. No. 9,302,134, which claims the benefit of U.S. Provisional Application No. 61/811,508 filed Apr. 12, 2013.

BACKGROUND OF THE INVENTION

1. Field of the Invention

The invention relates generally to the disposal of drugs. Specifically, this invention relates to methods, systems and apparatuses for the collection of excess, unwanted, tainted, recalled or expired drugs and rendering them in an unusable and non-retrievable form.

2. Description of the Related Art

The following descriptions and examples are not admitted to be prior art by virtue of their inclusion within this section.

Accepted and often employed methods of drug disposal include depositing drugs in the garbage or flushing them in the toilet or sink. There is growing concern that these methods of disposal can have undesired environmental effects. Indeed, recent studies have shown the presence of pharmaceutical compounds in the water supplies. Other methods of disposal include incineration and chemical digestions. Both of these methods are undesirable due to environmental and safety concerns. In particular, in the case of incineration, harmful agents can be released into the atmosphere as a result of burning the drug or its packaging. With chemical digestion, a chemical that is capable of dissolving a drug may be capable of causing harm to a human handler. Furthermore, within patient care centers such as, hospitals, ambulatory surgery centers and specialty procedure centers, drugs are frequently supplied for intravenous use. These drugs are often supplied in standard doses (i.e. the dose is not patient specific), which are frequently more than needed for a particular patient. This leads to unused drugs which have to be destroyed and rendered non-retrievable. Since intravenous drugs are in contact with a patient's intravenous line, they are considered contaminated and potentially represent a biohazard. So, in addition to the environmental issues, intravenous drugs also pose potential infectious risk to patients and clinical staff.

Some organizations which utilize, store and/or collect relatively large amounts of drugs, such as patient care facilities, pharmacies and law enforcement agencies, employ the services of a reverse distributor to dispose of drugs. A reverse distributor is an entity that is authorized by the United States Drug Enforcement Administration (DEA) to acquire controlled substances from DEA registrants in order to return them to a manufacturer or manufacturer's agent or for processing for disposal. Since the reverse distributor is a separate entity and apart from the DEA registrant, the transfer of the controlled substances necessitates that additional individuals handle the drugs, which incurs additional costs for disposal and increases the chance of drug diversion for illicit purposes. Furthermore, because drug disposal options are limited for individuals of the general public, prescription and over-the-counter drugs are often accumulate in individuals' medicine cabinets. This creates an opportunity for diversion for illicit purposes by teenagers or guests and accidental ingestion or overdose by young children.

It is therefore desirable to develop methods, apparatuses and systems with the ability to render drugs irretrievable and suitable for non-regulated waste disposal at the point of collection that poses no additional risk to the staff at the collection site. In addition, it would be advantageous for such methods, apparatuses and systems to neutralize any possible infectious agents and/or be employed without having to rely on the services of an outside party such as a reverse distributor.

SUMMARY OF THE INVENTION

Apparatuses, methods and systems are provided for rendering drugs unusable, irretrievable and suitable for non-regulated waste disposal. The following description of various embodiments of systems, methods and apparatuses is not to be construed in any way as limiting the subject matter of the appended claims.

Embodiments of methods for rendering a drug irretrievable include dispensing a predetermined amount of liquid into an interior cavity of a container, depositing the drug into the liquid within the interior cavity and subsequently dispensing into the interior cavity a absorbent material comprising crosslinkers which transforms the drug and the liquid together into a solid or semi-solid upon contact.

Embodiments of apparatuses include a receptacle, a stored supply of a absorbent material comprising crosslinkers and an input channel extending to an interior cavity of the receptacle, wherein the input channel is configured for substantially irretrievable access of drugs deposited in the interior cavity via the input channel. In addition, the apparatuses include a lower liquid level sensor disposed within the interior cavity at an elevation above a lower surface of the interior cavity and a user interface communicably coupled to the lower liquid level sensor such that the user interface receives one or more signals indicative of whether liquid is detected at the lower liquid level sensor. Furthermore, the apparatuses include an upper liquid level sensor disposed within the interior cavity of the receptacle at an elevation above the lower liquid level sensor and below an upper surface of the interior cavity and a means to release the stored supply of absorbent material comprising crosslinkers into the interior cavity of the receptacle. In some cases, the means for releasing the stored supply of absorbent material comprising crosslinkers is communicably coupled to the upper liquid level sensor such that the means receives a signal to release the absorbent material comprising crosslinkers into the interior cavity subsequent to detection of a liquid at the upper liquid level sensor. In addition or alternatively, the upper liquid level sensor may be communicably coupled to the user interface such that the user interface receives one or more signals indicative of whether liquid is detected at the upper liquid level sensor.

Embodiments of system include an analyzer for determining a composition, concentration and/or an amount of a drug dispensed in a container and further a dispenser communicably coupled to the analyzer such that information regarding the composition, concentration and/or amount of a drug determined at the analyzer and/or information regarding an amount of the agent needed to encapsulate a drug contained in the container based on analysis of the drug at the analyzer is received at the dispenser. The system further includes an automated device for moving the container from the analyzer in alignment with the dispenser.

BRIEF DESCRIPTION OF THE DRAWINGS

For a more complete understanding of the present invention, and the advantages thereof, reference is now made to the following descriptions taken in conjunction with the accompanying drawings, in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The disclosure herein relates generally to rendering drugs unusable, irretrievable and suitable for non-regulated waste disposal. As set forth in more detail below, the methods, apparatuses and systems described herein may have particular application for disposal of prescription drugs due to relatively new regulations in the United States related to the disposal of controlled substances by ultimate users, which the DEA defines as someone who possesses a controlled substance as the result of a lawful prescription. It is noted, however, that the methods, apparatuses, and systems described herein are not restricted to applications of prescription medications. In particular, the methods, apparatuses, and systems described herein may be used for the disposal of any drug. The term drug, as used herein, refers to a substance other than food that has a physiological effect when introduced into or applied onto the body. The term is inclusive to controlled substances, such as prescription medication and drugs used for nonmedicinal purposes, as well as over-the-counter drugs. As used herein, the term controlled substance refers to a drug or chemical substance whose possession and use are controlled by law. The term over-the-counter drug refers to medicines and therapeutic agents that do not require a prescription. The term disposal, as used herein, refers to the process of taking a substance to a location at which the substance is rendered for no use.

The Comprehensive Drug Abuse Prevention and Control Act of 1970 and the Controlled Substance Import and Export Act are collectively referred to as the Controlled Substances Act (CSA). The CSA is implemented and enforced by the Drug Enforcement Agency (DEA). The purpose of the CSA is to prevent, detect and eliminate the diversion of controlled substances and listed chemicals for illicit uses while maintaining an adequate supply of these materials for legitimate uses in areas of medicine, scientific research, and industry. The CSA requires the DEA to maintain a system for monitoring the manufacture, distribution, dispensing, importation and exportation of controlled substances. Central to this system are the methods that provide for the destruction of any unwanted, expired, recalled, tainted or unused controlled substances. For those entities that are registered to possess controlled substances with the DEA, the regulations regarding the handling, distribution, and destruction of controlled substances are well defined in the requirements of their registration. Not everyone who possesses a controlled substance, however, is required to register with the DEA. For example, a person may possess a controlled substance as a result of a lawful prescription and these individuals are also known as an 'ultimate user'. Under the United States Controlled Substances Act (CSA), an 'ultimate user' is defined as a person who has lawfully obtained, and possesses, a controlled substance for his own use or for the use of a member of his household or for an animal owned by him or by a member of his household.

As opposed to the well-established requirements for DEA registrants with regards to the handling, distribution and destruction of controlled substances, the CSA failed to contemplate that an ultimate user could possess unused controlled substances after receiving them as a result of a lawful prescription. While the ultimate user can legally possess a controlled substance, they are in violation of the CSA if they attempt to distribute, i.e., deliver or transfer, without appropriate DEA registration. Under the CSA, transfer of unused controlled substances by the ultimate user for the purpose of destruction or disposal would be considered unlawful distribution. Because the CSA did not have clear cut guidelines for disposal of controlled substances, there were limited options for their disposal. Ultimate users were permitted to destroy the drug themselves, surrender them to law enforcement or to the DEA.

Because of the availability of unused, outdated or unwanted prescription drugs, prescription drug abuse has reached epidemic proportions. To address this crisis, the Secure and Responsible Drug Disposal Act of 2010 was enacted on Oct. 12, 2010. This act is now referred to as the Disposal Act. The Disposal Act amended the CSA to permit an ultimate user to "deliver" a controlled substance "to another person for the purpose of disposal." The other person has to be authorized by the Attorney General and the disposal has to conform to exacting regulations to prevent the diversion of controlled substances. Another scenario addressed by the Disposal Act is that which occurs when an ultimate user dies while in lawful possession of a controlled substance. The Disposal Act authorizes any person who is lawfully entitled to dispose of the ultimate user decedent's property to transfer the ultimate user's controlled substance to another person for disposal. Further, within the Disposal Act, the DEA was given the ability to authorize long term care facilities (LCTF's) to dispose of controlled substances on the behalf of current or former residents of those facilities.

On Dec. 21, 2012, the DEA proposed new regulations related to the disposal of controlled substances by ultimate users. In the Federal Register, Vol. 77, No. 246, these proposed regulations are recorded. The objective of these new regulations is contained in the following statement:

> The goal of this proposed new part on disposal, consistent with Congress' goal in passing the Disposal Act, is to set controlled substance diversion prevention parameters that will encourage public and private entities to develop a variety of methods for collecting and destroying of controlled substances in a secure, convenient and responsible manner. Also, consistent with Congress's goal in passing the Disposal Act to decrease the amount of controlled substances introduced into the environment, particularly into the water.

Further objectives of the new proposals are illustrated by this statement:

> It is intended to maximize cost efficiency, voluntary participation and public accessibility while simultaneously promoting the secure and responsible disposal of controlled substances in order to prevent diversion.

The proposed regulation also provided for three voluntary options for the ultimate user controlled substance disposal. 1.) Take back events held by law enforcement agencies. 2.) Mail back programs to authorized collectors. 3.) Collection receptacles at retail pharmacies, the facilities of a manufacturer, distributor, law enforcement agency or reverse distributor. Oftentimes, as part of the processing of drugs for disposal or return to the manufacturer, reverse distributors will have to count and identify the contents of a collection bin. In the new proposals, the DEA clearly states that this should be avoided, as it would require individual identification of the contents, increase the number of hands though which controlled substances pass, and requires that the packages and inner liners remain open and exposed for extended periods of time. These factors greatly increase the risk of diversion and, when combined with the increased costs associated with such efforts, outweigh the potential benefit.

The proposed new regulations list required features of a collection receptacle. First, they must have a permanent outer container with a removable inner "liner". The outer container must have an opening large enough to allow controlled substances to be added but also not allow removal of contents of the inner liner. The opening to the inner liner must be capable of being locked when an authorized employee is not present. The size of the inner liner must be clearly marked as well as a unique identification number that would allow the inner liner to be tracked. Other requirements mentioned include security features such as securely fastening the receptacle to a wall, floor or unmovable countertop, displaying a sign that the receptacle only receives non-controlled drugs and Schedule II, III, IV or V controlled substances, and locating the receptacle in the immediate area where controlled substances are stored and an authorized employee is present. As set forth below, apparatuses and systems are described herein which fulfill these requirements.

The apparatuses and systems disclosed herein include one or more receptacles for receiving drugs and further include one or more stored supplies of one or more absorbent material comprising crosslinkers, wherein the apparatus and systems are adapted to release the absorbent material comprising crosslinkers into the one or more receptacles. In some cases, the apparatuses and systems described herein may include a single receptacle. In other cases, the apparatuses and systems described herein may include multiple receptacles. In either case, the apparatuses and systems described herein may be used and, in some embodiments, may be specifically configured to receive a single form of a drug or a variety of drug forms within the receptacle/s. Different forms of drugs which may be considered for collection in the receptacle/s include but are not limited to liquids, pills and patches. In some embodiments, the apparatuses and systems described herein may include separate receptacles for respectively collecting different forms of drugs. In other cases, the apparatuses and systems described herein may be configured to collect different forms of drugs in a single receptacle. In yet other embodiments, the apparatuses and systems described herein may include multiple receptacles for respectively collecting different groups of drug forms. For example, it is may be conducive to combine pill and patch drugs in one receptacle and liquid drugs in another receptacle. Other combinations may be considered as well. In general, the configuration and number of receptacles for a given apparatus or system as well its configuration to receive particular drug forms may depend on its design specifications to meet a given need.

In some cases, the apparatuses and systems described herein may be configured to receive a particular drug form or set of drug forms in a substantially irretrievable manner within a receptacle. For instance, an apparatus or system may be configured with an inlet channel which makes it difficult to route a suction tube therethrough. An example of such an inlet channel is the substantially curved liquid waste spillway described in more detail below in reference to the example collection apparatus depicted in FIG. 4. Other examples of inlet channels which may make it difficult to route a suction tube through is a spiral, convoluted or tortuous channel. In addition or alternatively, an apparatus or system may have an inlet with a relatively small opening, particularly small enough such that an individual cannot place a hand through it. For example, a pill receiving apparatus or system may have an inlet large enough to receive a range of pill sizes, but small enough such that an individual cannot place a hand through it. In addition, a patch receiving apparatus or system may have a slit inlet large enough to receive a range of sizes of patches, but small enough such that an individual cannot place a hand through it.

Additional configurations for apparatuses and systems suited for receiving a pill or patch drug may include a grinder (e.g., for a pill receptacle) and/or a shredder (e.g., for a patch receptacle) between the input port of the apparatus/system and a respective receptacle. In such cases, not only will inclusion of a grinder or shredder advantageously tear apart the drug, rendering it unusable and substantially irretrievable, but it may advantageously put the drug in a form which will react more efficiently with an agent added to the receptacle for denaturing, adulterating, disinfecting and/or destroying the drug. It is noted that the adaptations of the apparatuses and systems described herein to receive a particular drug form or set of drug forms in a substantially irretrievable manner within a receptacle are not limited to the aforementioned configurations. In particular, any adaptation known to those skilled in the art to render a drug substantially irretrievable from a container may be used in the apparatuses and systems described herein.

As noted above, the apparatuses and systems described herein include one or more stored supplies of one or more absorbent material comprising crosslinkers. The absorbent material comprising crosslinkers may be in a solid or liquid form. As set forth in more detail below, the absorbent material comprising crosslinker/s are used in the apparatuses, systems and method described herein to render drugs in the receptacle/s unusable, irretrievable and in a form suitable for non-regulated waste disposal, particularly for when the receptacles are removed from the apparatuses and systems described herein. In general, the absorbent material comprising crosslinkers/s transform a drug and an accompanying liquid residing within a receptacle together into a solid or semi-solid mass. Depending on whether the drug is in a liquid or solid form for such a transformation, the absorbent material comprising crosslinker/s used may be generally referenced as solidifying and/or encapsulating the drug, respectively. The term solidify, as used herein, refers to transformation of a liquid or a gas into a solid or semi-solid. The term encapsulate, as used herein, refers to enclosing or surrounding an entirety of a substance.

In general, absorbent materials comprising crosslinkers considered for use in the apparatuses, systems and method described herein are materials that can absorb and retain extremely large amounts of a liquid relative to their own mass. Examples of absorbent materials comprising crosslinkers include but are not limited to superabsorbent polymers, silica gel and clay materials. In some cases, a superabsorbent polymer may be preferred. Depending on the type and amount of crosslinkers included in an absorbent material comprising crosslinkers, the liquid absorbed by an absorbent material comprising crosslinkers and any object disposed therein are transformed into a solid or semi-solid mass. In particular, low density cross-linked absorbent materials comprising crosslinkers generally transform a liquid and any object disposed therein into a semi-solid mass, such as a gel. In contrast, relatively high density cross-linked absorbent materials comprising crosslinkers generally transform a liquid and any object disposed therein into a solid mass. Further to such dependency on the type and amount of cross-linker in an absorbent material comprising crosslinkers, it is noted that the degree of hardness of a solid mass produced by an absorbent material comprising crosslinkers may vary depending on the amount of the cross-linker in the absorbent material comprising crosslinkers. In particular, an absorbent material comprising crosslinkers may transform a liquid and any object disposed therein into a solid which deforms or indents when compressed or into a solid which does not.

In some cases, it may be advantageous for the apparatuses, systems and methods described herein to be configured to transform a drug and an accompanying liquid into a solid mass (i.e., versus a semi-solid mass) to make retrieving the drug more difficult, particularly if the drug was not denatured prior to or during the solidification/encapsulation process. In particular, a solid mass as compared to a semi-solid mass is at least construed to be more difficult to break open (i.e., via physical or liquefying means). Furthermore, any means used to open a solid mass may generally be harsher than those used to open a semi-solid mass and, thus, it may be more difficult to extract a usable form or a drug from a solid mass as compared to a semi-solid mass. Thus, a solid mass will more likely deter individuals from trying to extract a drug therefrom.

As such, in some cases, the absorbent material comprising crosslinkers used in the apparatuses, systems and methods described herein may include one or more crosslinkers of sufficient type and amounts to generate a solid mass and, in some cases, a single solid mass. In yet other embodiments, a drug may be denatured, adulterated or destroyed prior to or during the solidification/encapsulation process and, thus, forming a drug and an accompanying liquid into a solid mass (versus a semi-solid mass) may not be as advantageous in such embodiments. Despite the aforementioned advantages, it is noted that selection of an absorbent material comprising crosslinkers for the apparatuses, systems and method described herein is not limited to being dependent on whether a drug is denatured, adulterated or destroyed prior to or during a solidification/encapsulation process. In any case, as set forth below, the reaction of an absorbent material comprising crosslinkers with a drug and an accompanying liquid in the apparatuses, systems and methods described herein is generally conducted in a container/receptacle and the resulting solid or semi-solid mass is retained in the container/receptacle for disposal, providing a further measure to deter extraction of drugs.

In some cases, the apparatuses, systems and method described herein may use one or more agents to denature, adulterate and/or destroy drug/s within the receptacle/s. In addition or alternatively, the apparatuses, systems and method described herein may use one or more agents to neutralize/disinfect infectious materials within a receptacle (such as a drug or an accompanying liquid in the receptacle). Any of such agents may be integrated within the absorbent material comprising crosslinkers/s (i.e., admixed with the absorbent material comprising crosslinkers/s) or may be separate from the absorbent material comprising crosslinkers/s. To accommodate the latter case, the apparatuses and systems described herein may include one or more stored supplies of the agent/s and may be configured to dispense the agent/s in conjunction with the absorbent material comprising crosslinkers/s or prior to the absorbent material comprising crosslinkers/s.

The term denature, as used herein, refers to changing the chemical composition of a substance (i.e., versus inducing a physical change of the substance, such as its state of matter). Examples of denaturation processes which may be employed within the systems, apparatuses and methods described herein may include oxidation-reduction reactions and decomposition reactions, but other types of reactions may be considered. The term adulterate, as used herein, refers to debasing or making impure a substance by addition of other substance. The term destroy, as used herein, refers to rendering a substance into a useless form beyond repair or renewal. The term disinfect, as used herein, refers to the destruction of disease-carrying microorganisms. Example disinfecting agents include but are not limited to chlorine-releasing chemicals, such as but not limited to the one described below.

As noted above, agent/s capable of denaturing, adulterating, destroying and/or disinfecting may be, in some cases, integrated within the absorbent material comprising crosslinkers/s for the apparatuses, systems and method described herein. In particular embodiments, a chemical compound may be used that, when mixed with a liquid, adulterates any drug contained in a receptacle, kills any infectious materials in the receptacle, and converts the entire mixture into a solid or semi-solid mass that can be deposited into a landfill as non-regulated waste. An example of such a chemical compound is sodium dichloroisocyanurate (NaDCC or SDIC) mixed with a super absorbent polymer (SAP). When SDIC is dissolved in water or similar liquids, it hydrolyzes to form hypochlorous acid. As this occurs, high levels of chlorine are liberated which not only serves as a disinfectant but also oxidizes any compound dissolved within the liquid. Furthermore, the SAP absorbs the liquid and any materials dissolved or floating in the liquid and converts the entire mixture into a solid or semi-solid mass. Mixtures of SDIC and SAP are widely available commercially and can be acquired inexpensively. Some examples include, Liqui-Loc Plus™ and Isolyser®-LTS-Plus™. Liqui-Loc Plus™ is EPA approved and registered (EPA Registration Number 87708-

1-37549). It is noted that the absorbent materials comprising crosslinkers and agents used for denaturing, adulterating and destroying drugs and/or disinfecting infectious materials for the apparatuses, systems and methods described herein need not be limited to the noted examples of SAPs or SDIC. Rather, such citations have been provided as example compounds and agents which may be used in the apparatuses, systems and methods described herein.

In cases in which multiple receptacles are used to collect different forms of drugs, the apparatuses and systems described herein may include different denaturing, adulterating, destroying and/or disinfecting agents for each receptacle, depending on the drug form/s it is set to collect. For example, one or more agent/s which adulterate drugs and kills infectious materials may be particularly suitable for use with receptacles which collect intravenous drugs, while an agent which denatures drugs without neutralizing infectious materials may be suitable for receptacles which collect other types of liquid drugs, pills or patches.

As further noted above, the apparatuses and systems described herein are adapted to release the stored supplies of absorbent material comprising crosslinkers and, if applicable, denaturing, adulterating, destroying and/or disinfecting agent/s into the one or more collection receptacles. In general, the adaptation of the apparatuses and systems to release the absorbent material comprising crosslinkers and, if applicable, denaturing, adulterating, destroying and/or disinfecting agent/s may include a means by which to open the stored supplies of the absorbent material comprising crosslinkers and, if applicable, denaturing, adulterating, destroying and/or disinfecting agent/s such that the absorbent material comprising crosslinkers and the agent/s may be released into the cavities of the receptacles. One configuration includes one or more containers arranged within the receptacle with door/s, which when opened releases the chemicals. Alternatively, one more containers of absorbent material comprising crosslinkers and, if applicable, agent/s may be arranged exterior to the receptacle and the containers may be coupled to the receptacles by a valved pipe or chute, which when the valve is opened the contents of the container/s are released into the receptacle. Yet, another example of a releasing configuration is described in more detail below in reference to the example collection apparatus depicted in FIG. 3.

In any case, opening the stored supplies of absorbent material comprising crosslinkers and, if applicable, denaturing, adulterating, destroying and/or disinfecting agent/s may, in some embodiments, rely on manual operations by an operator of the apparatus or system. Alternatively, the apparatus or system may be automated to do so upon receipt of signal/s from a user interface of the system and/or upon receipt of signal/s from a liquid level sensor within the receptacle as described in more detail below. In some embodiments, the stored supplies of absorbent material comprising crosslinkers and, if applicable, denaturing, adulterating, destroying and/or disinfecting agent/s may be arranged near the upper surface of a receptacle. In some of such cases, the absorbent material comprising crosslinkers and, if applicable, denaturing, adulterating, destroying and/or disinfecting agent/s may be released into the receptacle by gravity after the one or more stored supplies are opened. In yet other embodiments, the absorbent material comprising crosslinkers and/or agent/s may be pumped to the cavity of the receptacle.

In either case, the timing of the release of the superabsorbent agent and/or the denaturing, adulterating, destroying and/or disinfecting agent/s may vary, depending on the design specifications and application of the apparatus/system. In some cases, the apparatus or system may be configured to treat a single deposit of one or more drugs. In particular, the apparatus or system may be configured to release a absorbent material comprising crosslinkers and, if applicable, one or more denaturing, adulterating, destroying and/or disinfecting agents after a single deposition to the receptacle. In other embodiments, however, the apparatus or system may be configured to release an absorbent material comprising crosslinkers and, if applicable, one or more denaturing, adulterating, destroying and/or disinfecting agents after drugs have accumulated in the receptacle. In any case, as noted above, if agents for denaturing, adulterating, destroying or disinfecting are used in the apparatus or system, they need not be released with the absorbent material comprising crosslinkers. In particular, they may alternatively be released from a separate storage and, in some cases, may be introduced into the receptacle prior to the absorbent material comprising crosslinkers.

In some cases, a receptacle may include a level sensor and upon the level sensor indicating drugs have amassed to a predetermined level within the receptacle, the absorbent material comprising crosslinkers and, if applicable, one or more agents may be released to mix with the drugs in the receptacle. In some cases, the means for releasing the stored supply of absorbent material comprising crosslinkers and, if applicable, one or more agents is communicably coupled to the upper liquid level sensor such that the means receives a signal to release the absorbent material comprising crosslinkers and, if applicable, the agent/s into the receptacle subsequent to detection of a liquid at the predetermined level by the liquid level sensor. In addition or alternatively, the liquid level sensor may be communicably coupled to a user interface of the apparatus or system such that the user interface receives one or more signals indicative of whether liquid is detected at the predetermined level by the liquid level sensor. In the latter cases, the release of the absorbent material comprising crosslinkers and, if applicable, the agent/s into the receptacle may be instigated by a user of the apparatus/system. Instigation by a user may, in some embodiments, be by manual means, such as but not limited to lifting a lid to a receptacle of the receptacle as described in more detail below in reference to FIGS. 1-5. In other cases, instigation by a user may be via input to the user interface to send a signal to activate an automated means to release the absorbent material comprising crosslinkers and, if applicable, the agent/s into the receptacle.

As noted above, in some cases, absorbent material comprising crosslinkers absorb and retain extremely large amounts of liquid and, thus, in some embodiments, a receptacle may be filled with a liquid prior to or subsequent to drugs being deposited in the receptacle. In some cases, a predetermined amount of liquid may be dispensed into an interior cavity of a receptacle. More specifically, an amount of liquid known/determined to sufficiently react with the subsequent addition of absorbent material comprising crosslinkers to solidify/encapsulate the entire contents of the receptacle may be dispensed into the receptacle prior to or subsequent to drugs being deposited in the receptacle. In cases in which liquid is dispensed in the receptacle prior to the deposition of drugs therein, the predetermined amount preferably takes into account that drugs will be added to the receptacle prior to the addition of the absorbent material comprising crosslinkers, increasing the volume which will be solidified/encapsulated in the receptacle.

The liquid dispensed into the receptacle prior to or subsequent to drugs being deposited in the receptacle may be any liquid which does not deteriorate and adversely react with the absorbent material comprising crosslinkers or the receptacle. In some cases, the liquid may be an aqueous solution and, in particular embodiments, the liquid may consist essentially of water. In view of such, the apparatuses and or systems may, in some embodiments, include a supply pipe coupled to a water source, such as but not limited to plumbing of a building in which the apparatus/system is arranged in. In cases in which the liquid is an aqueous solution, the ionic concentration of the aqueous solution may factor in the ability of the absorbent material comprising crosslinkers to absorb a liquid, particularly that a less ionic aqueous solution may absorb more than an aqueous solution with a higher ionic concentration. As such, in some cases, the liquid deposited into the receptacle may include deionized or distilled water and, in some cases, the apparatuses and/or systems described herein may include a means for deionizing and/or distilling water prior to it being introduced into a receptacle. In yet other embodiments, the liquid deposited in the receptacle may include a non-aqueous solution.

In any case, the receptacle may, in some cases, include two level sensors, a lower one for indicating a predetermined amount of liquid has been added to the receptacle and another for indicating drugs have amassed to a predetermined level within the receptacle as described above. In such cases, the lower level liquid sensor may be communicably coupled to a user interface of the apparatus/system such that the user interface receives one or more signals indicative of whether liquid is detected at the lower liquid level sensor. In general, the lower level liquid sensor may be arranged to detect liquid at an elevation above a lower surface of the interior cavity of the receptacle and the upper level liquid sensor may be arranged to detect liquid at an elevation above the lower level liquid sensor and below an upper surface of the interior cavity. In particular, the arrangement of the upper level liquid sensor to detect liquid at an elevation below an upper surface of the interior cavity of the receptacle is to accommodate for the formation of the solid or semi-solid mass formed by adding the absorbent material comprising crosslinkers to the receptacle, which generally swells to a volume larger than the liquid is it added to.

Example elevations for which the lower level and upper level liquid sensors may be arranged to detect liquid at may generally be indicative of less than one half of the receptacle volume and greater than one half of the receptacle volume, respectively. In particular embodiments, lower level and upper level liquid sensors may be arranged to detect liquid at levels indicative of ⅓ and ⅔ of the receptacle volume, respectively. Other liquid levels, however, may be considered for the both sensors, including levels which are both indicative of less than half the receptacle volume and levels which are both indicative of greater than half the receptacle volume.

In some cases, the receptacles and, optionally, the stored supplies of absorbent material comprising crosslinkers and/or agents may be arranged in a housing. The housing may serve as a fixed location at which disposable receptacles may be continually replaced. In particular, the solid or semi-solid mass resulting from the reaction of an absorbent material comprising crosslinkers and, possibly additional agents, with a drug and an accompanying liquid in a receptacle of the systems and methods described herein may be retained in the container for disposal. In yet other cases, a container may be configured to be opened to release the solid/semi-solid mass for subsequent disposal. In either embodiment, it is anticipated that a receptacle will be supplied to a user of the apparatus/system with its lid securely fastened and the absorbent material comprising crosslinkers and, if applicable, any additional agents preloaded into the receptacles and its release mechanism/s in place. Furthermore, the walls of the receptacle may, in some cases, be of a transparent material to verify a complete reaction (i.e., solidification/encapsulation) within the receptacle has occurred. In this manner, DEA guidelines may be met, specifically that all contents of the receptacle have been solidified/encapsulated can be witnessed and verified by two authorized individuals.

In some cases, the housings of the apparatuses described herein may be configured to receive/replace receptacles. For example, in embodiments in which operation of the apparatus or system is dependent on communications from one or more liquid level sensors within the receptacle, one or more sidewalls of the housing may include one or more electrical contacts respectively arranged to mate with electrical contacts on an outer surface of the receptacle which are coupled to the liquid level sensors within the receptacle. The electrical contacts along the sidewalls of the housing may be communicably coupled to a user interface of the apparatus/system and/or a means for releasing the stored supply of absorbent material comprising crosslinkers and/or agents, depending on the design specifications of the apparatus/system.

In any case, the housing may, in some embodiments, be fastened to a wall, floor or unmovable countertop. In some cases, the housing may be enclosable and, thus, the housing may serve as secondary containment to the receptacles and, if applicable, the stored supplies of absorbent material comprising crosslinkers and/or agents. In general, the housing may include inlets which respectively channel into the input ports of the one or more receptacles of the apparatus or system. In addition, the housing may include controls and a user interface for monitoring and affecting levels within the receptacles as well as the release of the absorbent material comprising crosslinkers and/or agents into the receptacles. In embodiments in which the housing is enclosable, the housing may include a locking mechanism, such as but not limited to a standard key lock, a combination lock, a combination keypad, or a card swipe mechanism. Other embodiments may allow user access after supplying biometric data such as a fingerprint or iris scan. In any of such cases, an enclosable housing may, in some embodiments, be configured to inhibit collection of drugs into the receptacles and/or inhibit release of the absorbent material comprising crosslinkers and/or agents into the receptacles until the enclosable housing is closed and/or locked. For example, apparatuses and systems described herein may be configured to block the input channels to the receptacles and/or prevent the mechanism used to release the absorbent material comprising crosslinkers and/or agents until the enclosable housing is closed and/or locked.

Further to the components noted above, the apparatus and systems disclosed herein may include a cleaning mechanism between at least one inlet of the outer housing and a respective input port of one of the receptacles. In general, the cleaning mechanism may serve to remove debris, particular remnants of drugs, within the inlet of the outer housing, a channel to the receptacle, an input port of the receptacle, and/or any shredder or grinder disposed within or in route to the receptacle. Any cleaning mechanism which is suitable to perform such a function may be used. Examples of cleaning mechanisms include but are not limited to a moveable brush and/or a fluid (i.e., liquid or gas) dispenser. Use of the cleaning mechanism may be manual or automated.

In general, any automated means or processes described herein may be facilitated by the use of program instructions stored in a storage medium of the apparatus or system. In general, the term "storage medium," as used herein, may refer to any electronic medium configured to hold one or more set of program instructions, such as but not limited to a read-only memory, a random access memory, a magnetic or optical disk, or magnetic tape. The storage medium may be on a computer within the apparatus or a remote computer, including a data cloud. The term "program instructions" may generally refer to commands within a program which are configured to perform a particular function, such as but not limited to receiving input, recording receipts of signals, sending output signals and determining whether to allow an apparatus to start an operation. Program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. Program instructions implementing the processes described herein may be transmitted over on a carrier medium such as a wire, cable, or wireless transmission link.

In some cases, it may be desirable or necessary (due to regulations) to analyze drugs deposited into the apparatuses and systems disclosed herein, particularly with respect to composition, concentration and/or quantity. Thus, in some embodiments, the apparatuses and systems described herein may include an analyzer for determining the composition and/or amount of the drug received by the apparatus or system. In some cases, the analyzer may be integrated into the apparatus comprising the receptacles. In other cases, however, the analyzer may be a distinct unit. In either embodiment, the apparatuses and systems described herein may be configured to draw a sample of a drug deposited into a collection site comprising the apparatus/system and route it to the analyzer.

In some cases, the collective site may be the receptacle itself. In other embodiments, it may be advantageous to analyze the drug prior to being mixed with the contents of the receptacle. As such, in some cases, the collection site may be a storage cell in the receptacle or, alternatively, may be a storage cell exterior to the receptacle such as but not limited to a region between an inlet of the outer housing and an input port of the receptacle. Additionally in such cases, the apparatus or system may include a means to release the drug from the storage cell into the main body of the receptacle upon identification and/or verification of the drug's composition, concentration and/or quantity. The means may include any of the configurations described above for the means for releasing the absorbent material comprising crosslinkers and, if applicable, any additional agents into the receptacle. Alternatively, a drug may be sampled and analyzed prior to being deposited into the apparatus or system.

In any case, the apparatuses and systems described herein may include an information recorder for documenting the reception and analysis of the drug analyzed by the analyzer. In addition, the apparatuses and systems described herein may include an overseeing authority information system operably connected to a network, wherein information stored in the information recorder may be reconciled against information stored in the overseeing authority information system. U.S. Pat. Nos. 6,868,344 and 7,184,897 describe a method, system and apparatus for collection, analysis and disposal of controlled substances which include an analyzer, an information recorder and access to an overseeing authority information system. The components and functional capability of the analyzer, information recorder and overseeing authority information system described in U.S. Pat. Nos. 6,868,344 and 7,184,897 are referenced for inclusion and use by the methods, apparatuses and systems described herein as if incorporated herein in their entirety.

Turning to the drawings, one example of a collection apparatus having the configurations described above is depicted in FIGS. 1-5. It is noted that the configuration of the collection apparatuses illustrated is merely exemplary. Many other configurations may be considered for the apparatuses and systems considered herein. For example, although FIGS. 1-5 illustrate a collection system with three receptacles, the apparatuses and systems described herein are not so limited. In particular, the apparatuses and systems described herein may include any number of receptacles, including a single receptacles or any plurality of receptacles. Furthermore, the apparatuses and systems described herein are not restricted to the specific means for dispensing absorbent material comprising crosslinkers into the receptacles as depicted and described in reference to FIGS. 1-6. As such, the apparatuses and systems described herein are not limited to the depictions in the drawings. Furthermore, it is noted that the drawings are not necessarily drawn to scale in that particular features may be drawn to a larger scale than other features to emphasize their characteristics.

Figure 1:
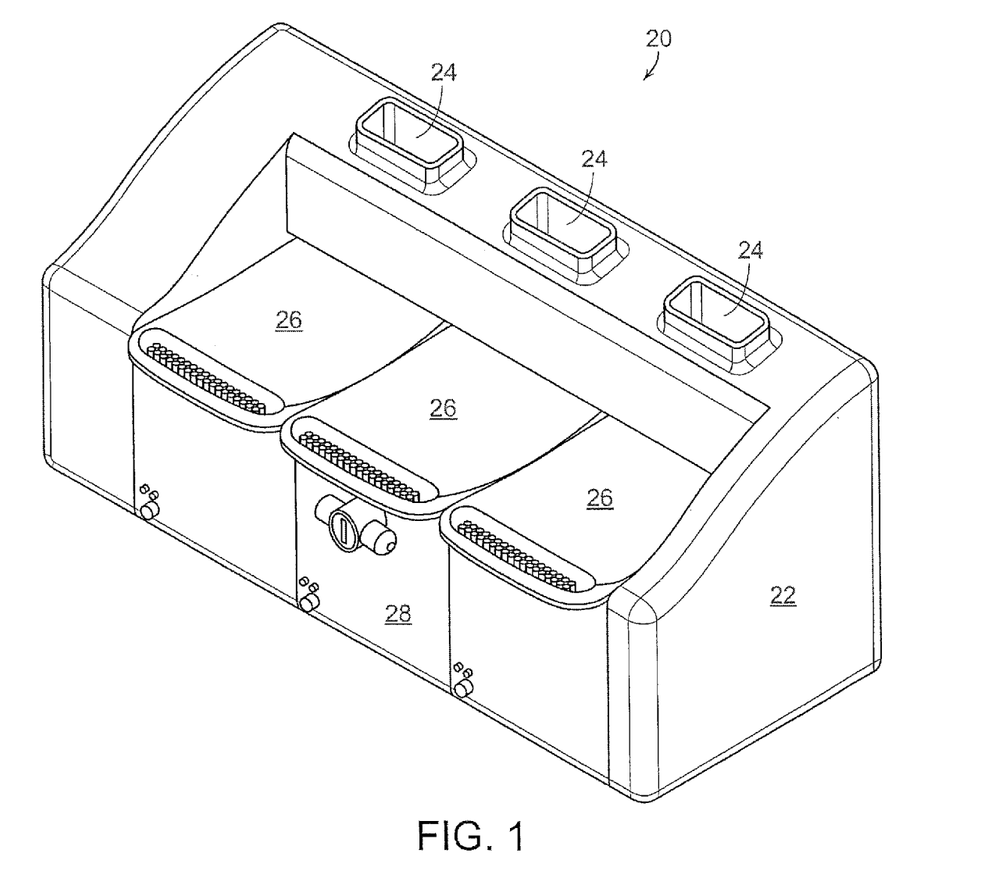
FIG. 1 is a perspective view of drug collection apparatus.
Figure 2:
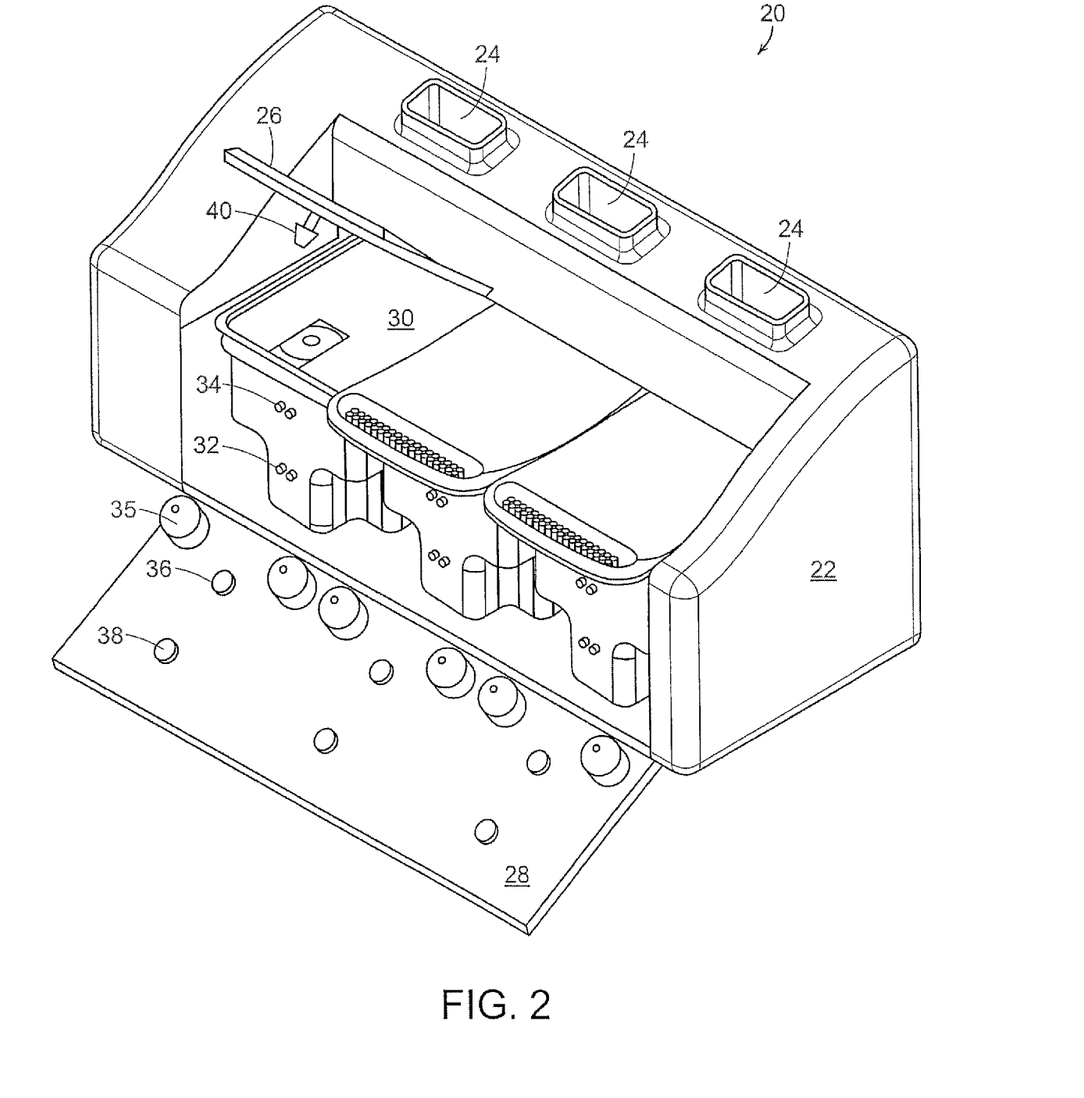
FIG. 2 is a view of the drug collection apparatus of FIG. 1 with its front door and a lid of one of the receptacles in the opened position.

FIG. 1 illustrates collection apparatus 20 including lockable outer housing 22 that securely houses three separate inner receptacles each for receiving a different drug form. For example, there may be a specified receptacle for drugs in each the pill, patch, and liquid form. As shown, outer housing 22 may include input ports 24 that connect to each of the inner receptacles, respectively. In some embodiments, each of input ports 24, receptacle lids 26, and/or respective portions of front door 28 may be labeled to receive a specific form of a drug. FIG. 2 illustrates the collection apparatus 20 with front door 28 open to access receptacles 30. Before placing an unused receptacle in outer housing 22, the receptacle may be prefilled with liquid (such as but not limited to water). In such cases, the receptacle may be prefilled at the entry port of the receptacle which is to align with the respective input port of outer housing 22 or any other entry port of the receptacle. Alternatively, the receptacle may be filled subsequent to being placed in outer housing 22. In such embodiments, the liquid may be supplied to the receptacle via respective port of input ports 24 or any other entry port to the receptacle. In any case, outer housing 22 may, in some embodiments, include a supply pipe coupled to a liquid supply to dispense the liquid within the receptacle. As noted above, the liquid supplied to the receptacle may be any liquid which does not deteriorate and adversely react with the absorbent material comprising crosslinkers or the receptacle. In some cases, the liquid may be an aqueous solution and, in particular embodiments, the liquid may consist essentially of water. In some cases, the liquid deposited into the receptacle may include deionized or distilled water. In yet other embodiments, the liquid deposited in the receptacle may include a non-aqueous solution.

In any case, the liquid may be filled to the level of liquid level sensor 32. Depending on the absorbent material comprising crosslinkers and, if applicable, one or more additional agents to be added to the receptacle, the minimum liquid level may be indicative of a volume of liquid needed to allow deposited drugs to be encapsulated within a solid or a semi-solid mass during the polymerization step that will be described later. In some cases, if the liquid level is below liquid level sensor 32, a visual or audible alarm will be activated. In some embodiments, power to other components of the apparatus, such as but not limited to a pill and patch shredder/grinder described in more detail below, may be interrupted until an adequate level is corrected and/or the alarm is inactivated.

In general, receptacles 30 may be configured to be fittingly arranged within individual compartments of outer housing 22. In some embodiments, receptacles 30 may include the same configuration (i.e., their configurations are not specific to the different compartments of outer housing 22). In other cases, however, receptacles 30 may be separately configured relative to the different compartments of outer housing 22 that they are to be received. In addition or alternatively, front door 28 of outer housing 22 may include one or more projections 35 for interfacing with respective alignment features of receptacles 30. Furthermore, front door 28 may include electrical contacts 36 and 38 to make contact with liquid level sensors 32 and 34 of each of receptacles 30 upon closing the door.

After proper alignment of receptacles 30 is achieved and front door 28 is closed, lids 26 for the receptacle are lowered. As this is done, protrusions 40 on the underside of each of lids 26 engage and penetrate engagement features 42 within the upper surface of each of receptacles. In general, each of engagement features 42 include an opening within a pliable material, which is arranged and sized to fittingly receive a respective of protrusions 40 when a respective of lids 26 is closed such that engagement feature 42 and the respective protrusion 40 become mechanically linked. As more clearly shown in FIGS. 3 and 5, each of receptacles 30 include release tab 44 extending from a stored supply of absorbent material comprising crosslinkers 46 (and, if applicable, one or more additional agents) to the opening within its engagement feature 42. In some cases, the stored supply of absorbent material comprising crosslinkers 42 (and, if applicable, one or more additional agents) may be a container, such as but not limited to a pouch, which is sealed by its union with upper lid 26.

Figure 3:
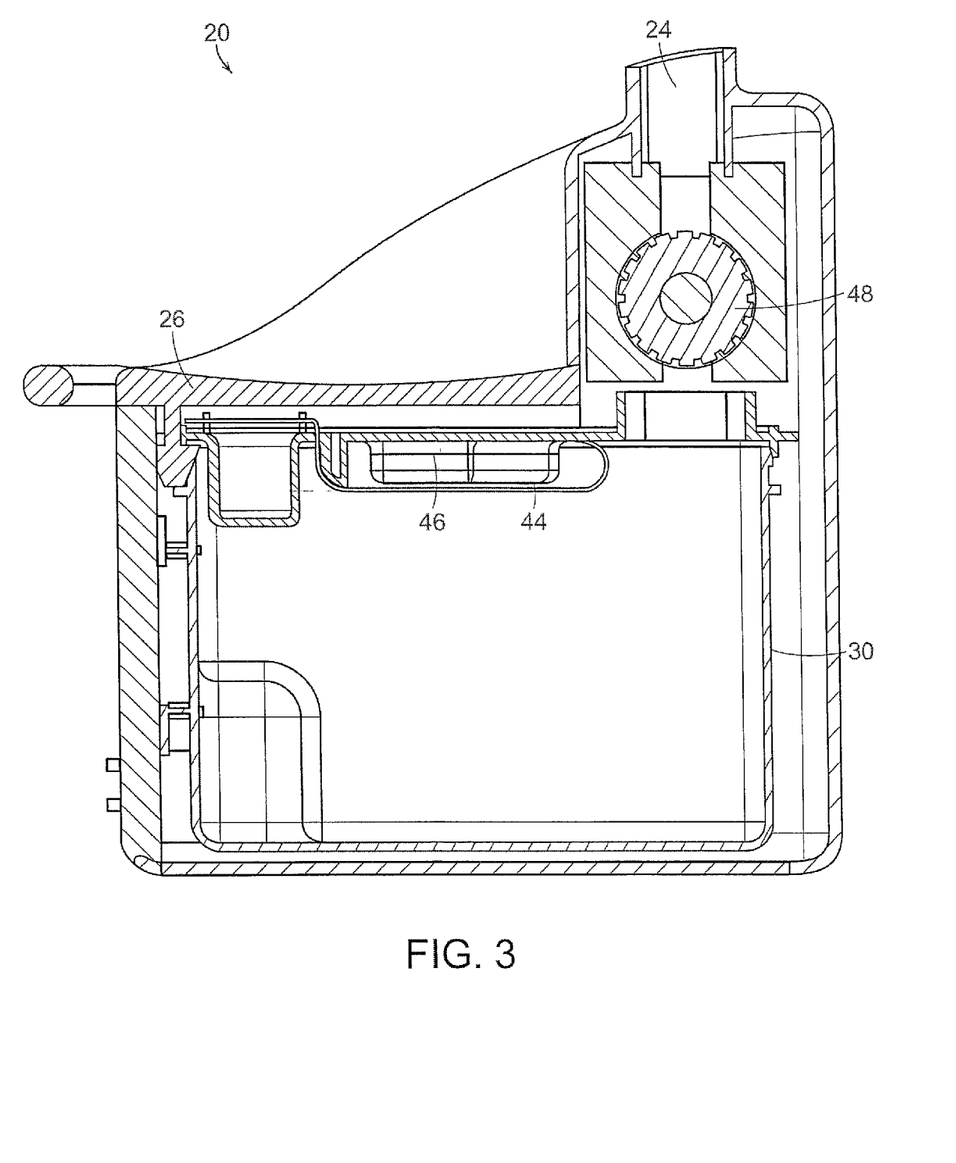
FIG. 3 is a cross-sectional view of the drug collection apparatus of FIG. 1 from front to back within one of the receptacles.

In any case, release tab 44, engagement feature 42 and protrusion 40 are collectively configured such that release tab 44 is pulled through a displacement sufficient to separate the container storing the absorbent material comprising crosslinkers from lid 26 to release stored supply of absorbent material comprising crosslinkers 46 into the interior cavity of its respective receptacle 30 when protrusion 40 is removed or is about to be removed from the opening of engagement feature 42 (i.e. when lid 26 is lifted). This feature advantageously prevents access to the contents of receptacles 30 without releasing the absorbent material comprising crosslinkers and, if applicable, additional agent/s to the receptacles. In general, as lid 26 is lifted higher, the portion of release tab 44 attached to protrusion 40 may be pulled through the opening of engagement feature 42 and removed from receptacle 30.

When liquid level sensor 32 indicates a minimum level of liquid is in receptacles 30 and further when front door 28 as well as lids 26 are closed, drugs may be deposited within apparatus 20. In some cases, input ports 24 and/or the channels extending therefrom may be configured to inhibit deposition of drugs into receptacles 30 until such conditions are met. For instance, input ports 24 and/or the channels extending therefrom may include a sliding barrier, a hinged flap or a lid which blocks input ports 24 and/or the channels extending therefrom and an automated means for moving the sliding barrier, hinged flap or lid when the aforementioned conditions are met. In yet other embodiments, input ports 24 and/or the channel extending therefrom may not include such prevention measures.

In any case, as noted above, the apparatuses and systems described herein may be configured to receive a particular drug form or set of drug forms in a substantially irretrievable manner within a receptacle. As such, input ports 24 may, in some embodiments, be relatively small, particularly small enough such that an individual cannot place a hand through them. Furthermore, the size and/or shape of input ports 24 may vary depending on the drug which is to be received therein. For example, the input port extending to the pill collection receptacle may have a circular or elliptical inlet large enough to receive a range of pill sizes, while the input port extending to the patch collection receptacle may have a narrow cylindrical or elliptical slit inlet large enough to receive a range of sizes of patches. Conversely, an input port extending to a liquid collection receptacle may include an opening configured for a liquid drug to be poured and/or injected therein. In any of such cases, input ports 24 and/or the channels extending therefrom may be additionally or alternatively configured with decreasing dimensions or a one-way flap mechanism so that solid-form drugs (such as pills or patches) will be irretrievable once deposited.

Figure 4:
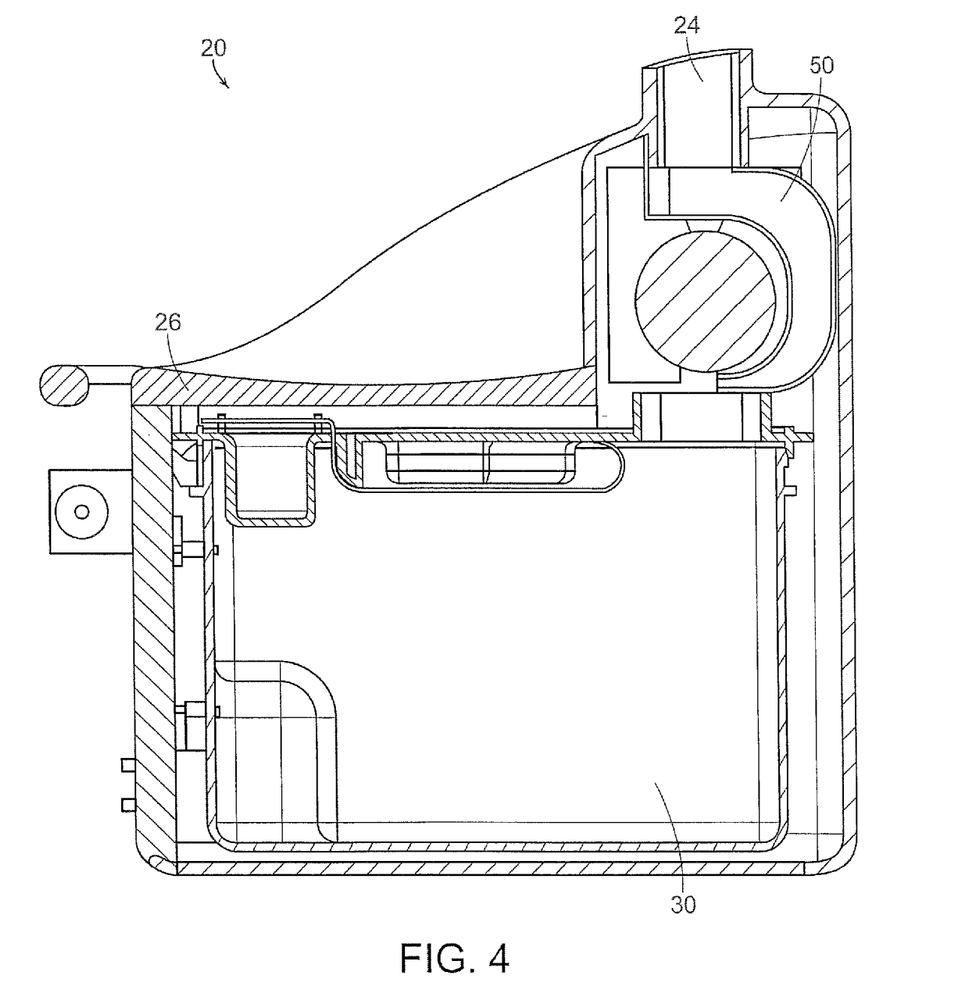
FIG. 4 is a cross-sectional view of the drug collection apparatus of FIG. 1 from front to back within another one of the receptacles
Figure 5:
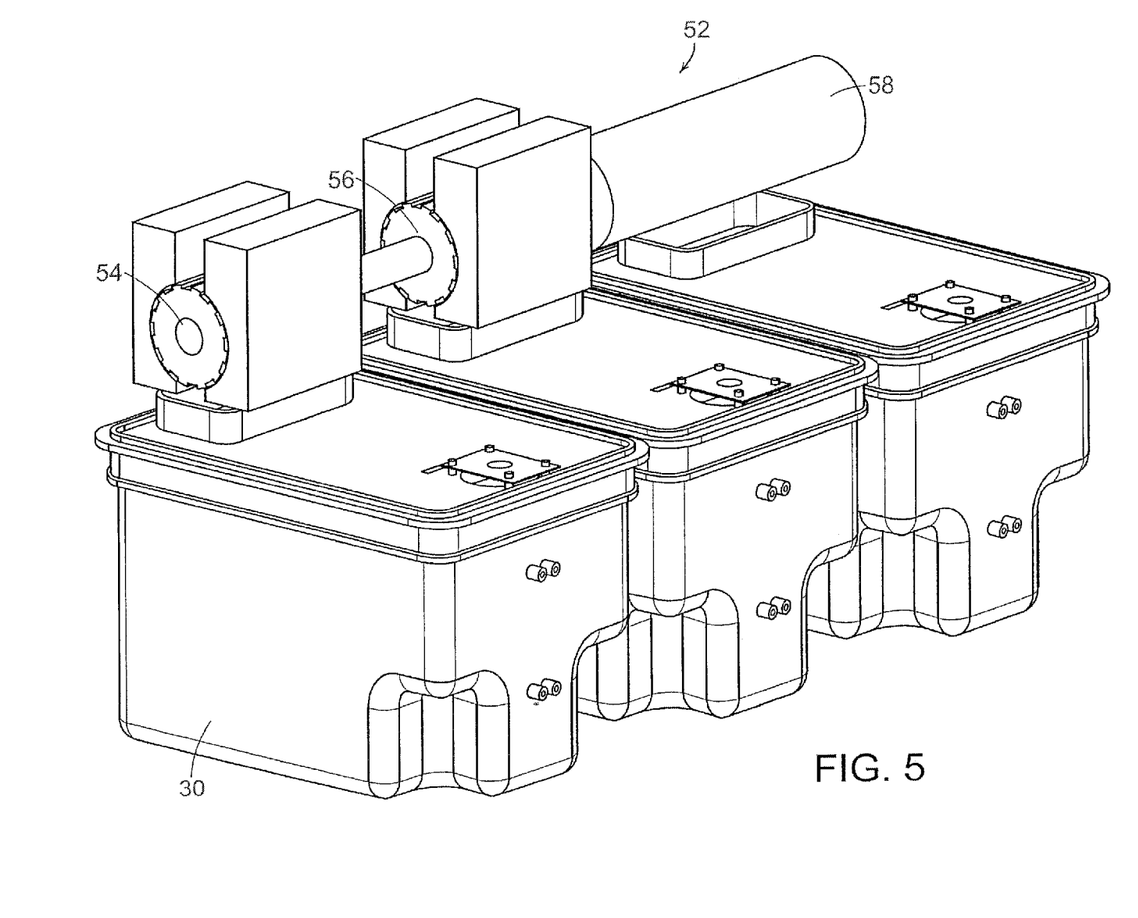
FIG. 5 is a perspective view of the drug collection apparatus of FIG. 1 without its outer housing and with a combination assembly of a grinder, shredder and a shaft extending from the grinder and shredder, each over a respective receptacle.

As noted above, additional or alternative measures may be taken to insure a drug is deposited in an irretrievable manner with a receptacle. FIGS. 3-5 illustrate examples of additional or alternative measures for apparatus 20. In particular, FIG. 3 illustrates an example configuration of apparatus 20, specifically a cross-sectional view of apparatus 20 within one of receptacles 30 extending from the front to the back of the apparatus. As shown in FIG. 3, apparatus 20 may include a grinder/shredder 48 above a receptacle to convert pills into powder or to shred patches before dropping into the receptacle. As another example, FIG. 4 illustrates a cross-sectional view of apparatus 20 within another one of receptacles 30 extending from the front to the back of the apparatus. As shown in FIG. 4, apparatus 20 may include circuitous inlet channel 50 extending from input port 24 to prevent retrieval of drugs deposited into an underlying receptacle, specifically to make it difficult to route a suction tube through the inlet channel. Other examples of inlet channels which may make it difficult to route a suction tube include but are not limited to spiral, convoluted and tortuous channels.

FIG. 5 illustrates a perspective view of apparatus 20 without outer housing 22 having a combination assembly 52 of grinder 54 above a pill receptacle, shredder 56 above a patch receptacle, and shaft 58 extending from grinder 52 and shredder 54 above a liquid receptacle. In general, circuitous inlet channel 50 from FIG. 4 may be configured to route around shaft 58. Although not shown in FIGS. 3-5, apparatus 20 may include a cleaning mechanism between any one or more of input ports 24 and respective input ports of receptacles 30. In general, the cleaning mechanism may serve to remove debris, particular remnants of drugs, within input ports 24, inlet channels extending from input ports 24 to receptacles 30, input ports of receptacles 30, grinder 54 and/or shredder 56. Any cleaning mechanism which is suitable to perform such a function may be used. Examples of cleaning mechanisms include but are not limited to a moveable brush and/or a fluid (i.e., liquid or gas) dispenser. Use of the cleaning mechanism may be manual or automated.

As drugs accumulate in a particular receptacle of apparatus 20, the liquid level in the receptacle rises until it activates the liquid level sensor 34. Once liquid level sensor 34 is activated, either the absorbent material comprising crosslinkers and, if applicable, one or more agents will be automatically released to mix with the drugs in the receptacle or an visual or audible alarm will display on the outer housing notifying a user to instigate the release of the absorbent material comprising crosslinkers and, if applicable, one or more agents into the receptacle. Instigation by a user of apparatus 20 may be by lifting lid 26 to cause protrusion 40 to pull release tab 44 a displacement sufficient to separate the container storing the absorbent material comprising crosslinkers from lid 26 as described above. Each inner receptacle will have its own alarm and/or liquid level display, allowing the user to take actions to appropriately address the alarm notification. Once the contents of the absorbent material comprising crosslinkers and, if applicable, one or more agents are emptied into receptacle 30, the chemical reaction with resultant solidification, and possibly disinfection and/or destruction of the receptacle's contents occurs almost instantaneously. Receptacle 30 can be removed and, in some cases, the opening of engagement feature 42 can then be sealed. However, the latter may not be necessary, as the container content will now exist in a solid mass form. In some cases, the walls of receptacle 30 may be of any material that is transparent enough to verify that a complete reaction (i.e. solidification) has occurred. In accordance with DEA guidelines, this result can be witnessed and verified by two authorized individuals. After this, receptacle 30 with its destructed contents can be deposited in any common waste receptacle.

Figure 6:
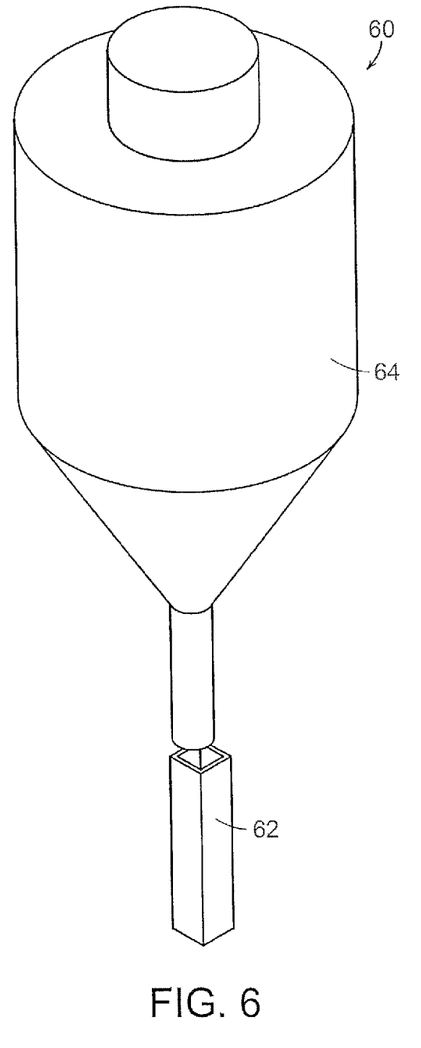
FIG. 6 is a cross-sectional view illustrating the introduction of a absorbent material comprising crosslinkers into a cuvette by an auger located within a hopper.

FIG. 6 is an illustrative embodiment of system 60 in which analysis and verification of a drug occurs prior to it being solidified and, possibly disinfected and/or denatured, and rendered irretrievable. In particular, a liquid drug is deposited into a container 62, such as but not limited to a cuvette, and is taken by an automatic mechanism to an analysis station. After analysis, if data pre-entered by the depositor matches the analysis results, the drug-filled container 62 is moved beneath dispenser 64 and the auger within the hopper dispenses the absorbent material comprising crosslinkers, and if applicable, one or more additional agents in an amount sufficient to solidify, and possibly disinfect, denature, and/or destroy that volume of liquid controlled substance.

In some cases, the reaction induced within a drug-filled container may be consistent with a preceding analysis event. More specifically, dispenser 64 may be communicably coupled to the analyzer such that information regarding the composition, concentration and/or amount of a drug determined at the analyzer is received at the dispenser. Dispenser 64 may, in some cases, be configured to determine an amount of the agent needed to encapsulate a drug contained in the container based on the received information. In addition or alternatively, the analyzer may be configured to make such a determination and send it to the dispenser. In particular, dispenser 64 may be communicably coupled to the analyzer such that information regarding an amount of the agent needed to encapsulate a drug contained in the container based on analysis of the drug at the analyzer is received at the dispenser. In any case, the drug-encapsulated container can be collected and disposed of in the garbage at any time after that.

In conclusion, the methods, apparatuses and systems described herein provide authorized personnel to receive drugs from ultimate users and destroy and dispose of them in an environmentally conscious fashion without the involvement of outside parties. In addition, the methods, apparatuses and systems described herein also provide for the disposal and disinfection of liquid drugs in hospitals and other patient care settings. In the preceding discussion, it has been shown that a desirable collection receptacle and system can accommodate the deposition and destruction of drugs collected from ultimate users. It has also been shown that this collection receptacle and system is capable of destroying the drugs on site and without the need for further involvement of outside parties in the disposal process. Further, it has been shown that such a collection receptacle and system can be utilized in a hospital setting to handle all forms of unwanted controlled substances—pills, patches and liquids. Also, in the hospital setting, it has been shown that applying a method of solidification, and possibly disinfection, denaturation and/or destruction of liquid drugs after an analysis and verification process had been performed on said sample may be desirable.

It is noted that although the disclosure provided herein focuses on the solidification, and possibly disinfection, denaturation and/or destruction of drugs, the methods, apparatuses and systems may be used for solidification, and possibly disinfection, denaturation and/or destruction of substances other than drugs. Examples of substances which may have particular application include but are not limited to non-drug controlled substances, such as controlled chemicals or materials including controlled chemicals. In such cases, the absorbent material comprising crosslinkers and, if applicable one or more additional agents used for the methods, apparatuses and systems described herein is selected based on its ability to react with the controlled substance without producing hazardous substances and/or conditions.

What is claimed:

1. A system, comprising:
   a container;
   an analyzer for determining a composition, concentration and/or an amount of a drug contained in the container;
   a dispenser communicably coupled to the analyzer such that information regarding the composition, concentration and/or amount of a drug determined at the analyzer is received at the dispenser;
   a receptacle;
   a means to release the drug from the container into the receptacle upon identification and/or verification of the composition, concentration and/or amount of the drug at the analyzer; and
   a stored supply of an agent to disinfect, neutralize, denature, adulterate and/or destroy the drug, wherein the stored supply of the agent is coupled to the dispenser, and wherein the dispenser is configured to release the agent into the receptacle subsequent to receiving the information regarding composition, concentration and/or amount of the drug.

2. The system of claim 1, wherein the analyzer sends the information regarding composition, concentration and/or amount of the drug to the dispenser subsequent to matching the information with data pre-entered into the analyzer.

3. The system of claim 1, wherein the dispenser is further configured to determine, prior to releasing the agent into the container, an amount of the agent needed to disinfect, neutralize, denture, adulterate and/or destroy the drug contained in the container based on the received information regarding composition, concentration and/or amount of the drug.

4. The system of claim 1, wherein the analyzer is configured to:
   determine an amount of the agent needed to disinfect, neutralize, denture, adulterate and/or destroy the drug contained in the container based on the determined composition, concentration and/or amount of the drug in the container; and transmit the determined amount of the agent to the dispenser.

5. The system of claim 1, further comprising:
an input channel extending to an interior cavity of the receptacle, wherein the input channel is configured for substantially irretrievable access of drugs deposited in the interior cavity via the input channel.

6. The system of claim 1, further comprising a means for drawing a sample of the drug in the container and routing the sample to the analyzer.

7. The system of claim 1, further comprising an information recorder for documenting the reception and analysis of drugs analyzed by said analyzer.

8. The system of claim 7, further comprising an overseeing authority information system operably connected to a network, wherein information stored in said information recorder is reconciled against information stored in said overseeing authority information system.

9. A system, comprising:
a container;
a stored supply of an absorbent material comprising crosslinkers;
a dispenser coupled to the stored supply for releasing the absorbent material comprising crosslinkers into the container; and
an analyzer communicably coupled to the dispenser, wherein the analyzer is configured to:
determine a composition, concentration and/or an amount of a drug contained in the container;
determine an amount of the absorbent material comprising crosslinkers needed to encapsulate the drug contained in the container based on the determined composition, concentration and/or amount of the drug in the container; and
transmit the determined amount of the absorbent material comprising crosslinkers to the dispenser.

10. The system of claim 9, wherein the analyzer is configured to:
compare the determined composition, concentration and/or amount of the drug in the container with data pre-entered into the analyzer; and
upon detecting a match between the determined composition, concentration and/or amount of the drug and the pre-entered data, determine an amount of the absorbent material comprising crosslinkers needed to encapsulate the drug contained in the container.

11. The system of claim 9, wherein the absorbent material comprising crosslinkers further comprises an agent to disinfect, neutralize, denature, adulterate and/or destroy the drug.

12. The system of claim 9, further comprising:
a stored supply of an agent distinct from the stored supply of the absorbent material comprising crosslinkers, wherein the agent is configured to disinfect, neutralize, denature, adulterate and/or destroy the drug; and
a different dispenser coupled to the stored supply of the agent for releasing the agent into the container.

13. The system of claim 9, further comprising an input channel extending to an interior cavity of the container, wherein the input channel is configured for substantially irretrievable access of drugs deposited in the interior cavity via the input channel.

14. The system of claim 9, further comprising a means for drawing a sample of the drug contained in the container and routing it to the analyzer.

15. The system of claim 9, further comprising an information recorder for documenting the reception and analysis of drugs analyzed by said analyzer.

16. The system of claim 15, further comprising an overseeing authority information system operably connected to a network, wherein information stored in said information recorder is reconciled against information stored in said overseeing authority information system.

17. A system, comprising:
a container;
an analyzer for determining a composition, concentration and/or an amount of a drug contained in the container;
a dispenser communicably coupled to the analyzer such that information regarding the composition, concentration and/or amount of a drug determined at the analyzer is received at the dispenser; and
a stored supply of an absorbent material comprising crosslinkers, wherein the stored supply of the absorbent material comprising crosslinkers is coupled to the dispenser, and wherein the dispenser is configured to release the absorbent material comprising crosslinkers into the container subsequent to receiving the information regarding composition, concentration and/or amount of the drug.

18. The system of claim 17, wherein the analyzer sends the information regarding composition, concentration and/or amount of the drug to the dispenser subsequent to matching the information with data pre-entered into the analyzer.

19. The system of claim 17, wherein the dispenser is further configured to determine, prior to releasing the absorbent material comprising crosslinkers into the container, an amount of the absorbent material comprising crosslinkers needed to encapsulate the drug contained in the container based on the received information regarding composition, concentration and/or amount of the drug.

20. The system of claim 17, wherein the absorbent material comprising crosslinkers further comprises an agent to disinfect, neutralize, denature, adulterate and/or destroy the drug.

21. The system of claim 17, further comprising:
a stored supply of an agent distinct from the stored supply of the absorbent material comprising crosslinkers, wherein the agent is configured to disinfect, neutralize, denature, adulterate and/or destroy the drug; and
a different dispenser coupled to the stored supply of the agent for releasing the agent into the container.

22. A system, comprising:
a container;
an analyzer for determining a composition, concentration and/or an amount of a drug contained in the container;
a dispenser communicably coupled to the analyzer such that information regarding the composition, concentration and/or amount of a drug determined at the analyzer is received at the dispenser; and
a stored supply of an agent to disinfect, neutralize, denature, adulterate and/or destroy the drug, wherein the stored supply of the agent is coupled to the dispenser, and wherein the dispenser is configured to release the agent into the container subsequent to receiving the information regarding composition, concentration and/or amount of the drug.

23. The system of claim 22, wherein the analyzer sends the information regarding composition, concentration and/or amount of the drug to the dispenser subsequent to matching the information with data pre-entered into the analyzer.

24. The system of claim 22, further comprising:
a stored supply of an absorbent material comprising crosslinkers distinct from the stored supply of the agent; and
a different dispenser coupled to the stored supply of the absorbent material for releasing the absorbent material into the container.

25. A system, comprising:
a container;
an analyzer for determining a composition, concentration and/or an amount of a drug contained in the container;
a dispenser communicably coupled to the analyzer such that information regarding the composition, concentration and/or amount of a drug determined at the analyzer is received at the dispenser;
a receptacle;
a means to release the drug from the container into the receptacle upon identification and/or verification of the composition, concentration and/or amount of the drug at the analyzer; and
a stored supply of an absorbent material comprising crosslinkers, wherein the stored supply of the absorbent material comprising crosslinkers is coupled to the dispenser, and wherein the dispenser is configured to release the absorbent material comprising crosslinkers into the receptacle subsequent to receiving the information regarding composition, concentration and/or amount of the drug.

26. The system of claim 25, wherein the analyzer sends the information regarding composition, concentration and/or amount of the drug to the dispenser subsequent to matching the information with data pre-entered into the analyzer.

27. The system of claim 25, wherein the dispenser is further configured to determine, prior to releasing the absorbent material comprising crosslinkers into the receptacle, an amount of the absorbent material comprising crosslinkers needed to encapsulate the drug contained in the receptacle based on the received information regarding composition, concentration and/or amount of the drug.

28. The system of claim 25, wherein the analyzer is configured to:
determine an amount of the absorbent material comprising crosslinkers needed to encapsulate the drug contained in the receptacle based on the determined composition, concentration and/or amount of the drug in the container; and
transmit the determined amount of the absorbent material comprising crosslinkers to the dispenser.

29. The system of claim 25, wherein the absorbent material comprising crosslinkers further comprises an agent to disinfect, neutralize, denature, adulterate and/or destroy the drug.

30. The system of claim 25, further comprising:
a stored supply of an agent distinct from the stored supply of the absorbent material comprising crosslinkers, wherein the agent is configured to disinfect, neutralize, denature, adulterate and/or destroy the drug; and
a different dispenser coupled to the stored supply of the agent for releasing the agent into the container.

31. The system of claim 25, further comprising an input channel extending to an interior cavity of the receptacle, wherein the input channel is configured for substantially irretrievable access of drugs deposited in the interior cavity via the input channel.

32. A system, comprising:
a container;
a stored supply of an agent to disinfect, neutralize, denature, adulterate and/or destroy the drug;
a dispenser coupled to the stored supply for releasing the agent into the container; and
an analyzer communicably coupled to the dispenser, wherein the analyzer is configured to:
determine a composition, concentration and/or an amount of a drug contained in the container;
determine an amount of the agent needed to disinfect, neutralize, denature, adulterate and/or destroy the drug contained in the container based on the determined composition, concentration and/or amount of the drug in the container; and
transmit the determined amount of the agent to the dispenser.

33. The system of claim 32, wherein the analyzer is configured to:
compare the determined composition, concentration and/or amount of the drug in the container with data pre-entered into the analyzer; and
upon detecting a match between the determined composition, concentration and/or amount of the drug and the pre-entered data, determine an amount of the agent needed to encapsulate the drug contained in the container.

34. The system of claim 32, further comprising an information recorder for documenting the reception and analysis of drugs analyzed by said analyzer.

35. The system of claim 34, further comprising an overseeing authority information system operably connected to a network, wherein information stored in said information recorder is reconciled against information stored in said overseeing authority information system.

* * * * *